(12) United States Patent
Link

(10) Patent No.: US 8,486,144 B2
(45) Date of Patent: Jul. 16, 2013

(54) ENDOPROSTHESIS HAVING A PLUG-IN CONNECTION AND IMPROVED ROTARY PROTECTION

(75) Inventor: Helmut D. Link, Hamburg (DE)

(73) Assignee: Deru GmbH, Norderstedt (DE)

( * ) Notice: Subject to any disclaimer, the term of this patent is extended or adjusted under 35 U.S.C. 154(b) by 81 days.

(21) Appl. No.: 13/060,258

(22) PCT Filed: Aug. 21, 2009

(86) PCT No.: PCT/EP2009/006096
§ 371 (c)(1),
(2), (4) Date: Feb. 22, 2011

(87) PCT Pub. No.: WO2010/020429
PCT Pub. Date: Feb. 25, 2010

(65) Prior Publication Data
US 2011/0160858 A1 Jun. 30, 2011

(30) Foreign Application Priority Data
Aug. 22, 2008 (DE) ............ 20 2008 011 178 U

(51) Int. Cl.
*A61F 2/28* (2006.01)
(52) U.S. Cl.
USPC ................. 623/16.11; 623/11.11
(58) Field of Classification Search
CPC .......................................... A61F 2/28
USPC .............. 623/11.11, 16.11, 20.32–20.36
IPC ............................................. A61F 2/28, 2/38
See application file for complete search history.

(56) References Cited

U.S. PATENT DOCUMENTS

| 5,137,535 | A | * | 8/1992 | Keller | 623/20.36 |
| 6,500,207 | B1 | * | 12/2002 | Keller | 623/20.15 |

(Continued)

FOREIGN PATENT DOCUMENTS

| DE | 19712758 | 10/1998 |
| DE | 202004019264 | 4/2006 |

(Continued)

OTHER PUBLICATIONS

Austria Search Report dated Apr. 2, 2009 in related Application No. DE202008011178.1 filed Aug. 22, 2008, 4 pages.

(Continued)

*Primary Examiner* — Jason-Dennis Stewart
(74) *Attorney, Agent, or Firm* — Dentons US LLP

(57) ABSTRACT

The invention relates to an endoprosthesis, particularly for the at least partial replacement of a long bone, comprising a plug-in connection for connecting a shaft (2) to another part (1) of the prosthesis, wherein the plug-in connection (3) comprises an axial projection (33) and a socket (34). According to the invention, provision is made that a radial transverse channel (53) is provided on one part of the plug-in connection (3), said radial transverse channel (53) engaging behind the plug-in connection and having a center axis (55) that is offset (d) relative to the axis (56) of a transverse bore (52) arranged on the other part of the plug-in connection, and a clamping element (6) which is to be inserted into the transverse channel (53) and whose point (62), in the inserted state, engages in the transverse bore (52). In this way, it is possible to achieve an effective securing action even in the event of an unfavorable tolerance pairing, without adversely affecting the sensitive projection itself.

20 Claims, 3 Drawing Sheets

U.S. PATENT DOCUMENTS

2004/0193268 A1* 9/2004 Hazebrouck ............... 623/16.11
2009/0193268 A1 7/2009 Kreiner et al.
2009/0312840 A1* 12/2009 Morrey ...................... 623/20.11

FOREIGN PATENT DOCUMENTS

| DE | 202005014269 U1 | 1/2007 |
|----|----|----|
| EP | 0474015 | 8/1991 |
| EP | 1088531 | 4/2001 |
| EP | 1421919 | 5/2004 |
| WO | WO98/04215 | 2/1998 |
| WO | WO2007/028832 | 3/2007 |

OTHER PUBLICATIONS

DE19712758 published Oct. 8, 1998, bibliographic data downloaded from espacenet.com, abstract only in English, 1 page.

DE202004019264 published Apr. 27, 2006, bibliographic data downloaded from espacenet.com, abstract only in English, 1 page.

EP0474014 published Aug. 19, 1991, abstract translated into English by Google at epo.org, 1 page.

EP1088531 published Apr. 4, 2001, bibliographic data downloaded from espacenet.com, abstract only in English, 2 pages.

EP1421919 published May 26, 2004, bibliographic data downloaded from espacenet.com, abstract only in English, 1 page.

International Preliminary Report of Patentability in related International Application No. PCT/EP09/06096, filed Aug. 21, 2009, 17 pages.

International Search Report in related International Application No. PCT/EP09/06096, filed Aug. 21, 2009, 3 pages.

DE 202005014269 published Jan. 18, 2007, abstract only in English, downloaded from espacenet.com 1 page.

* cited by examiner

ENDOPROSTHESIS HAVING A PLUG-IN CONNECTION AND IMPROVED ROTARY PROTECTION

CROSS REFERENCE TO RELATED APPLICATIONS

The present application claims the benefit of PCT International Application No. PCT/EP09/06096, filed 21 Aug. 2009, which claims the benefit of German Application No. 202008011178.1, filed 22 Aug. 2008; each of which are incorporated herein by reference in their entireties.

The invention relates to an endoprosthesis, particularly for the at least partial replacement of a long bone, comprising a plug-in connection for connecting a shaft to another part of the prosthesis, wherein the plug-in connection comprises an axial projection and a socket.

Endoprostheses, particularly for the treatment of extensive bone defects, are usually made up of several parts and have an elongate shaft-like prosthesis part. Arranged at the end of the prosthesis part there are means for permitting a connection to further prosthesis parts or to a remaining natural bone section. It must be borne in mind that, particularly in the case of endoprostheses for replacement of long bones, in particular for the femur, substantial forces occur as a result of lever effects at the connection sites. The same applies to connection sites between segments of the prosthesis. The connections used there must therefore withstand considerable loads. Not only must they safely transfer substantial forces over long periods of time, they must also be practically free of play and, if so required, must also be able to be separated again in order to permit an exchange of segments.

It is known to connect multi-part prostheses using a plug-in connection with a cone (DE 202004019264 U1). To provide protection against unwanted rotation, a separate anti-rotation means is provided in the form of axially projecting anti-rotation stubs. The connection is produced during the operation by means of the cones of the plug-in connection being inserted one inside the other with sufficiently great force. However, it has been found that the force needed to achieve a secure connection cannot always be applied under all circumstances. This is particularly the case when there are unfavorable intraoperative conditions, such as poor accessibility to the operating site. It is therefore known to use securing devices in order to secure the cone. This is usually done using a securing screw which, in a first known embodiment, is arranged with its axis parallel to the axis of the cone and thus pulls together the components that are to be connected. A second embodiment principally involves acting on the flank of the cone by means of a transversely arranged screw (DE 202005014269 U1; EP 1088531 A1). In both cases, the design of the prosthesis parts becomes complicated, and weakening occurs, specifically in the area where substantial forces have to be able to be transferred.

The object of the invention is to provide an endoprosthesis of the first-mentioned type with improved securing of the plug-in connection.

The solution according to the invention lies in an endoprosthesis having the features of the independent claim. Advantageous developments form the subject matter of the dependent claims.

In such an endoprosthesis, intended particularly for the at least partial replacement of a long bone and comprising a plug-in connection for connecting a shaft to another part of the prosthesis, wherein the plug-in connection comprises an axial projection and a socket, provision is made, according to the invention, that a transverse channel is provided on one part of the plug-in connection, said transverse channel engaging behind the projection, and a clamping element which is to be inserted into the transverse channel and whose point, in the inserted state, engages in the transverse bore. Engaging behind the projection is here to be understood as a position on the shaft side of the projection, for example on a flange of the projection. An offset is understood as an oriented distance between the axis of the transverse channel and of the transverse bore, with nominal dimensions when the projection is inserted fully into the socket. The distance value is oriented such that, when the projection is not yet fully pushed into the socket of the plug-in connection, the offset has a higher value, which decreases until the projection is finally received completely in the socket. An important point here is that the offset remains positive even when the projection is fully inserted; it should not become zero, nor should it even be negative.

The invention is based on the recognition that, with the clamping element in the transverse channel, a reaction force clamping the projection in the direction of the socket can be exerted by acting on the transverse bore, and, by virtue of the claimed positive axial offset, the desired clamping action is achieved even in the event of a deviation from the nominal dimension within the tolerance range, specifically even in the event of an unfavorable tolerance pairing. In this way, secure clamping is permitted even under unfavorable circumstances. The cone connections that are often used for plug-in connections of this kind have the particular feature that, even with just slight tolerances in the cone diameter, considerable differences in respect of the depth of insertion arise because of the small cone angle required for the self-locking. Because of these differences, a sufficient securing action could not be achieved by a simple grub screw inserted into a transverse bore; in some cases this would even lead to a rearward movement and, consequently, to a loosening of the cone connection. The invention has now recognized that this problem of the plug-in connection, arising from unavoidable tolerances, can be elegantly solved by means of the transverse channel and the transverse bore having a positive axial offset. This ensures that the desired clamping action is achieved even with unfavorable tolerances.

The offset chosen is expediently so small that the transverse channel overlaps the transverse bore even at the minimum depth of insertion of the projection into the socket. This also provides safety in the case when, in the event of over-tolerance, the projection can be pushed into the socket only with difficulty or not completely. It has proven useful that the axial offset measures at least 0.3 mm and is not greater than 1.2 mm, preferably being between 0.5 mm and 0.8 mm.

As regards the diameter, more precisely the core diameter, of the transverse channel, it is advantageously at least twice as great, preferably three times as great, as the difference between the maximum and minimum depth of insertion. This ensures that a sufficient overlapping between the transverse channel and the transverse bore is achieved independently of the actual depth of insertion, such that the clamping action according to the invention can still be obtained. The transverse bore is advantageously designed such that it tapers conically. It is generally designed as a blind hole, although this is not absolutely essential. The conicity is relatively large and is preferably over 30°, preferably lying between 45 and 75°. This conicity ensures that, by the engagement of the clamping element in the transverse bore, said clamping element comes to lie on that side of the conicity directed toward the other part of the plug-in connection. Upon further insertion of the clamping element, the projection is driven farther into the socket.

It has been proven useful to design the tip of the clamping element with a displacement surface, which is preferably designed as a wedge tip. If the clamping element itself has a conicity, it is independent of any conicity of the transverse bore, or, if such is present, is further strengthened thereby.

In most cases it will suffice if only one transverse channel is arranged with an axially offset transverse bore. However, provision can also be made for two or more to be provided. This is recommended particularly if the transverse channel is arranged in an anti-rotation stub, and if such a transverse channel is likewise arranged in what is in most cases a diametrically opposite further anti-rotation stub. The provision of two (or more) affords the advantage of a greater securing action. However, there can then be a risk of static overdetermination, which can result in distortion or overloading. To avoid this, provision can be made that at least one clamping element, preferably the second (or further) clamping element, has an elastic tip. The danger of distortion during tightening is thereby avoided, and the desired additional securing action is achieved. An advantage is that, if the first clamping element fails, a securing action is still achieved by the clamping element with the elastic tip. Although a slight play may then exist, this nevertheless has the advantage of signaling the defect of the first clamping element to the patient and to the treating physician, without their having to worry about a total failure of the securing action.

The elasticity of the tip is advantageously provided by a covering, for example made of an elastic material such as rubber or of another elastic material with high biocompatibility, for example certain types of polyethylene.

The invention is explained in more detail below on the basis of an advantageous illustrative embodiment and with reference to the attached drawing, in which.

Figure 3A:
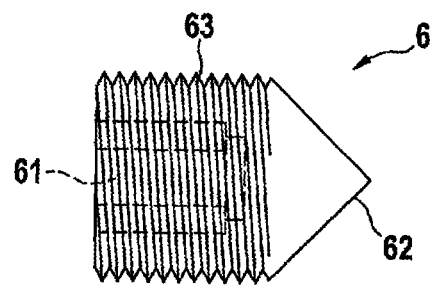
Figure 4:
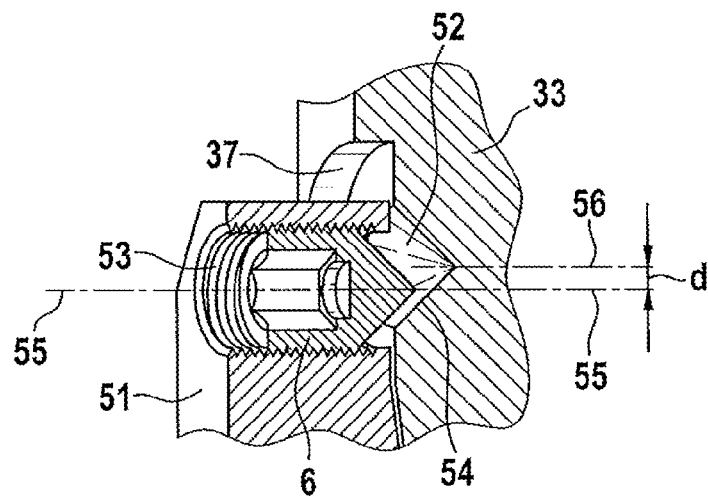
Figure 5:
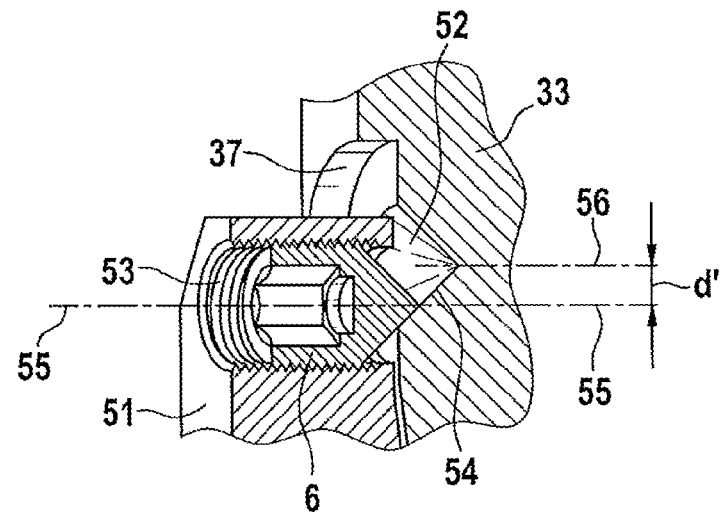
Figure 6:
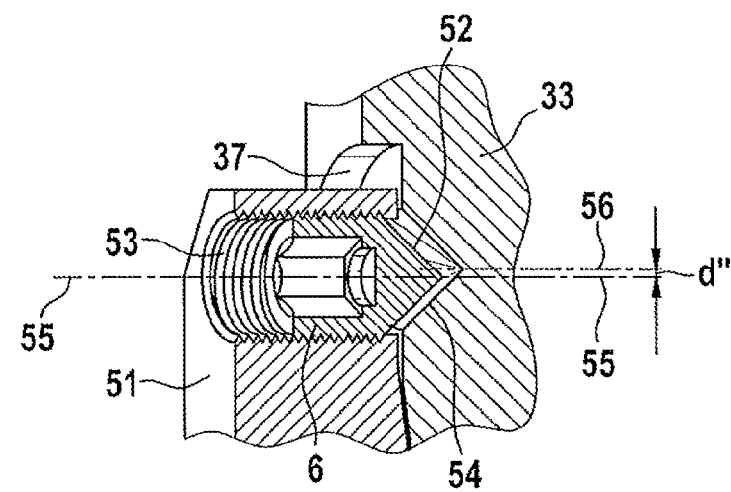

FIGS. 3a,b show illustrative embodiments of clamping elements;

FIG. 4 shows a partial cross-sectional view illustrating an axial offset in a normal position;

FIG. 5 shows a partial cross-sectional view illustrating the axial offset in a maximum position, and FIG. 6 shows a partial cross-sectional view illustrating the axial offset in a minimum position.

The invention is illustrated using the example of an endoprosthesis designed for the partial replacement of the femoral bone in the area of the upper end thereof. The prosthesis is made up of two segments, namely an upper prosthesis part 1, with a joint pin 10 for receiving a ball head (not shown) as part of an artificial hip joint, and a shaft 2 which is to be inserted into a bone marrow cavity of the remaining part of the natural femur. The prosthesis part 1 and the shaft 2 are connected to each other by a plug-in connection 3. A separate anti-rotation means 4 is also provided on the plug-in connection.

The plug-in connection 3 and the anti-rotation means 4 are explained in more detail below with reference to FIG. 2. The upper end of the shaft 2 is seen in the left-hand part of the figure. A thickened flange 30 with an outwardly directed end face 31 is arranged on the upper end of the shaft. A cone-like projection 33 arranged on the axial continuation of the axis of the shaft 2 extends from said end face 31. The cone is cut off at its front end 35 to form a truncated cone. Moreover, pocket-like recesses 37 are formed on the radial surface of the flange 30 and extend from the end face 31 to the shaft 2. They have a transverse bore 52 oriented with respect to the center axis of the shaft 2. The transverse bore 52 is designed as a blind hole with a conicity 54 at the bottom thereof.

Figure 1:
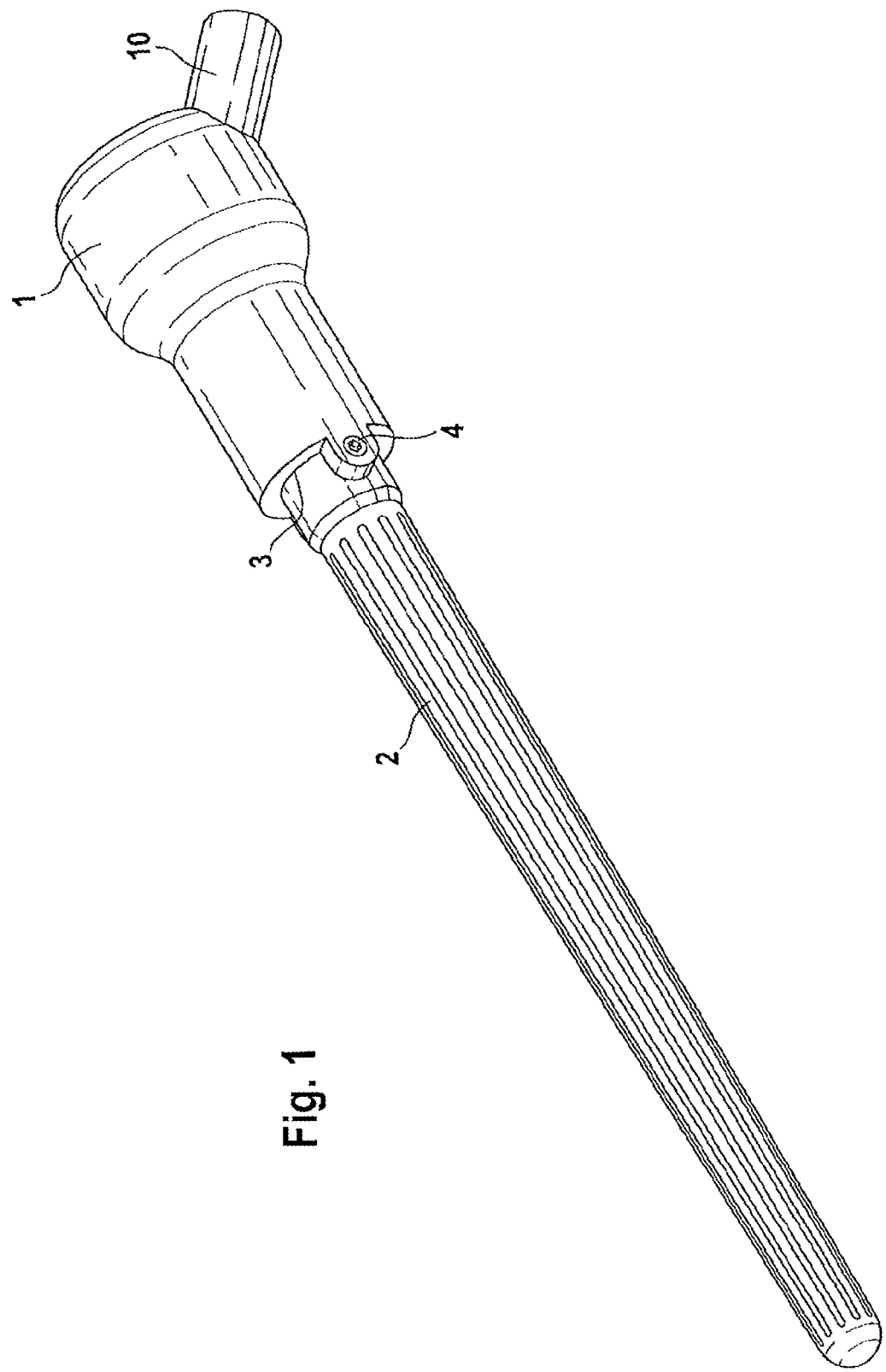
FIG. 1 shows a perspective view of an endoprosthesis according to an illustrative embodiment of the invention.
Figure 2:
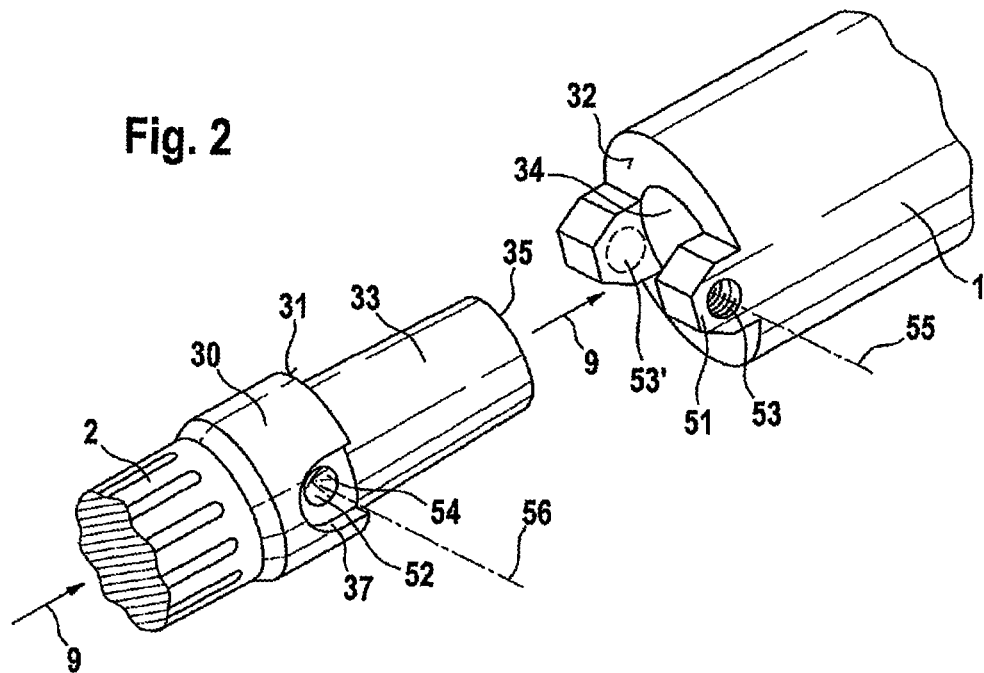
FIG. 2 shows an enlarged partial view of a plug-in connection of two segments of the endoprosthesis according to FIG. 1.

The right-hand half of FIG. 2 shows the lower end of the prosthesis part 1 forming the femoral head. It is of a generally cylindrical shape and has an end face 32 at its lower end. A receiving bore 34, the inside wall of which runs conically inward, is arranged centrally in this end face 32. The dimensions of the receiving bore 34 are tailored to the projection 33 of the shaft part 2 such that the projection 33 can be pushed almost completely into the receiving bore 34 until only a small clearance (typically with values of 0.75 mm) remains between the end faces 31 and 32. In each case, the depth of the receiving bore 34 is dimensioned such that the end faces 31, 32 come to lie one on the other before the tip 35 of the projection comes to lie on the bottom of the socket 34. The distance, structurally predetermined by the dimensions, between the outer end 35 and the end face 32 forms a measure of the depth of insertion.

Two axially projecting anti-rotation stubs 51 lying diametrically opposite each other are also formed on the prosthesis part 1. In the assembled state, they cooperate with the corresponding recesses 37 in the flange 30 of the shaft 2. The width of the anti-rotation stubs 51 is tailored to the width of the recesses 37 such that, allowing for play necessary for easy insertion, the shaft 2 is secured against rotation relative to the prosthesis part 1.

A transverse channel 53 extending transversely with respect to the insertion direction 9 is arranged in the anti-rotation stub. This transverse channel 53 has an inner thread into which a clamping element 6 can be screwed. The center axis of the transverse channel 55 intersects the insertion direction 9 at a right angle. Accordingly, a transverse bore 52 is formed on the radial surface inside the recess 37. This transverse bore 52 is designed as a blind hole with a conicity 54 at the bottom thereof. The tip of the conicity defines a center axis 56. It will be noted that the conicity does not necessarily have to be full and instead it can also be cut off as a truncated cone; this does not in any way change the position of the center axis 56.

The clamping element 6 is shown in FIG. 3. It is designed similarly to a grub screw, with a cylindrical main body whose jacket surface carries an outer thread 63. The latter is dimensioned such that it engages in the inner thread of the transverse channel 53. On one end face, a hexagonal depression 61 is formed, which serves as a socket for a wrench as actuating tool. The opposite end face 62 is designed as a pointed cone. The cone angle is advantageously such that it corresponds to the cone angle determining the conicity 54 of the transverse bore 52.

The cooperation between the transverse channel 53 and the transverse bore 52 is explained in more detail with reference to FIGS. 4 to 6. These show a partial cross section through the plug-in connection in the inserted state, i.e. the projection 33 is located in the socket 34. It has been pushed in until a firm fit is achieved by virtue of the conical shape. In the illustrative embodiment shown, the dimensions are chosen such that there is a remaining clearance of 1.25 mm between the end faces 31, 32. According to the invention, the axial offset d between the center axis 55 of the transverse channel 53 and the center axis 56 of the transverse bore 52 is chosen such that, in this position of the plug-in connection, which is defined as the normal position, there is an axial offset of 0.75 mm. This has the effect that the clamping element 6, when screwed into the transverse channel 51, comes to lie with a center on the flank of the conical part of the transverse bore 52 directed toward the end face 31. By turning the clamping element 6 in, a force driving the projection 33 farther into the receiver 34 is exerted on the projection 33. The plug-in connection is thereby clamped.

On account of tolerances during production and/or due to not completely correct insertion, it is possible for tolerances to arise in respect of the position of the prosthesis parts 1, 2. The situation shown in FIG. 5 arises in the event of an unfavorable tolerance pairing, namely projection 33 at the upper tolerance limit and receiver 34 at the lower tolerance limit, or incomplete insertion by the operator. Here, the depth of insertion of the plug-in connection 3 is less, such that there is a clearance of 1.7 mm between the end faces 31, 32. The actual axial offset d' is then 1.2 mm. Taking the axial offset into account, the diameter of the transverse bore 52 is in this case chosen such that the center line 55 still comes to lie in the area of the flank directed toward the end face 31. Thus, when the clamping element 6 is pushed in, the tip thereof engages with this flank, as a result of which the desired clamping effect is achieved. In this case too, the desired clearance-free fit is achieved even in the event of unfavorable tolerance pairing or incomplete insertion.

FIG. 6 shows the opposite case of tolerance pairing, namely with a projection 33 at the lower tolerance limit and a receiver 34 at the upper tolerance limit. Here, the depth of insertion of the plug-in connection is greater than the one provided structurally for the normal position (see FIG. 4). The choice according to the invention of the axial offset ensures that in this case too, with a clearance of 0.8 mm, there is still a positive actual axial offset d" of 0.3 mm. Therefore, secure clamping is also ensured in this very unfavorable case of tolerance pairing.

Figure 3B:
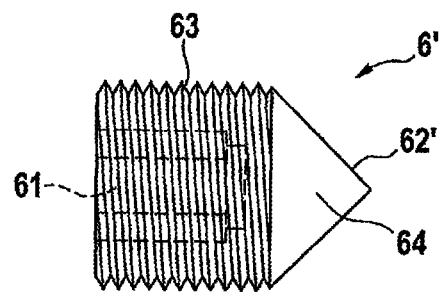

FIG. 3b shows a variant of the clamping element 6'. It differs from the clamping element 6 shown in FIG. 3a mainly in terms of the fact that a covering 64 of elastic material is arranged on the tip 62. The elastic material can be a rubber-like material or highly biocompatible, highly elastic polyethylene. In order to increase the elasticity, the entire tip 62' can be made of the elastic material. Such a design of the clamping element 6' is of advantage if, in a second (or further) anti-rotation stub, a corresponding transverse channel 53' (see broken line in FIG. 2) a corresponding transverse bore is provided in the associated recess (not shown). With the elastic design at the tip, the clamping element 6' effectively counteracts the danger of static overdetermination and, consequently, of overloading or of poorer positioning. The axial offset of the second transverse channel 53' is advantageously greater than that of the first transverse channel 55. This affords the advantage of making available a fallback position in which there is a slight and therefore appreciable but not critical play.

The invention claimed is:

1. A prosthesis, for the at least partial replacement of a long bone, comprising:
a plug-in connection for connecting a shaft to a first part of the prosthesis, wherein the plug-in connection comprises an axial projection and a socket, characterized in that a radial transverse channel is provided on a first portion of the plug-in connection, said radial transverse channel engaging behind the plug-in connection and having a center axis that is positively offset relative to an axis of a transverse bore provided on a second part of the plug-in connection; and
a clamping element designed for insertion into the transverse channel, wherein a point of the clamping element, in the inserted state, engages in the transverse bore.

2. The prosthesis of claim 1, wherein the axial offset chosen is at least so large that it is positive even at a maximum depth of insertion, wherein the maximum depth is a depth at which an end face of the shaft lies on an end face of the first portion.

3. The prosthesis of claim 1, wherein the axial offset chosen is at most so large that the transverse channel overlaps the transverse bore even at a minimum depth of insertion, wherein the minimum depth of insertion is a depth to which the axial projection may be inserted into the transverse bore as a result of at least one of an unfavorable tolerance pairing between the axial projection and the transverse bore, and incorrect insertion of the axial projection into the transverse bore.

4. The prosthesis of claim 1, wherein the axial offset measures at least 0.3 mm.

5. The prosthesis of claim 1, wherein a core diameter of the transverse channel is at least twice as great as the difference between minimum and maximum depth of insertion, wherein the maximum depth is a depth at which an end face of the shaft lies on an end face of the first portion and the minimum depth is a depth to which the axial projection may be inserted into the transverse bore as a result of at least one of an unfavorable tolerance pairing between the axial projection and the transverse bore, and incorrect insertion of the axial projection into the transverse bore.

6. The prosthesis of claim 1, wherein a bottom of the transverse bore tapers conically.

7. The prosthesis of claim 6, wherein the bottom of the transverse bore tapers conically at an angle of greater than 30°.

8. The prosthesis of claim 6, wherein the bottom of the transverse bore tapers conically at an angle of between 45° and 75°.

9. The prosthesis of claim 1, wherein the transverse channel s provided in an axially parallel projecting first anti-rotation stub of the plug-in connection.

10. The prosthesis of claim 9, wherein the transverse channel is a first transverse channel and a second transverse channel is provided in a second anti-rotation stub.

11. The prosthesis of claim 10, wherein the second anti-rotation stub is diametrically opposite the first anti-rotation stub.

12. The prosthesis of claim 10, wherein the second transverse channel has another axial spacing.

13. The prosthesis of claim 12, wherein the axial spacing of the second transverse channel is greater than the axial spacing of the first transverse channel.

14. The prosthesis of claim 1, wherein the point is designed as a wedge-shaped displacement surface.

15. The prosthesis of claim 1, wherein the tip of the clamping element is elastic.

16. The prosthesis of claim 15, wherein the tip is designed with a covering made of elastic material.

17. The prosthesis of claim 16, wherein the elastic material is a highly elastic polyethylene material.

18. The prosthesis of claim 1, wherein the axial offset measures between 0.5 mm and 0.8 mm.

19. The prosthesis of claim 1, wherein a core diameter of the transverse channel is at least three times as great as the difference between minimum and maximum depth of insertion, wherein the maximum depth is a depth at which an end face of the shaft lies on an end face of the first portion and the minimum depth is a depth to which the axial projection may be inserted into the transverse bore as a result of at least one of an unfavorable tolerance pairing between the axial projection and the transverse bore, and incorrect insertion of the axial projection into the transverse bore.

20. The prosthesis of claim 1, wherein the axial offset measures not greater than 1.2 mm.

* * * * *